United States Patent
Hwang et al.

(10) Patent No.: US 10,517,814 B2
(45) Date of Patent: Dec. 31, 2019

(54) SUNSCREEN COMPOSITIONS WITH NATURAL WAXES FOR IMPROVED WATER RESISTANCE

(71) Applicant: Edgewell Personal Care Brands, LLC, Chesterfield, MO (US)

(72) Inventors: Hui-Ing Donna Hwang, Leonia, NJ (US); Alexander Naranjo, Essex Junction, VT (US); Patricia Lynn Scott, Union, NJ (US)

(73) Assignee: EDGEWELL PERSONAL CARE BRANDS, LLC, Chesterfield, MO (US)

( * ) Notice: Subject to any disclaimer, the term of this patent is extended or adjusted under 35 U.S.C. 154(b) by 0 days.

(21) Appl. No.: 15/886,976

(22) Filed: Feb. 2, 2018

(65) Prior Publication Data

US 2018/0221271 A1 Aug. 9, 2018

Related U.S. Application Data

(60) Provisional application No. 62/454,206, filed on Feb. 3, 2017.

(51) Int. Cl.

| | |
|---|---|
| *A61K 8/06* | (2006.01) |
| *A61K 8/36* | (2006.01) |
| *A61K 8/37* | (2006.01) |
| *A61K 8/55* | (2006.01) |
| *A61K 8/92* | (2006.01) |
| *A61Q 17/04* | (2006.01) |

(52) U.S. Cl.
CPC ............... *A61K 8/922* (2013.01); *A61K 8/06* (2013.01); *A61K 8/361* (2013.01); *A61K 8/37* (2013.01); *A61K 8/55* (2013.01); *A61K 8/925* (2013.01); *A61Q 17/04* (2013.01); *A61K 2800/5922* (2013.01)

(58) Field of Classification Search
CPC ... A61K 8/06; A61K 8/36; A61K 8/37; A61K 8/55; A61K 8/92
See application file for complete search history.

(56) References Cited

U.S. PATENT DOCUMENTS

| | | |
|---|---|---|
| 6,409,997 B1 | 6/2002 | Castro |
| 2002/0098158 A1 | 6/2002 | Singh |
| 2006/0153783 A1* | 7/2006 | Ehlis .................... C07D 251/18 424/59 |

FOREIGN PATENT DOCUMENTS

| | | |
|---|---|---|
| DE | 19756921 A1 | 6/1999 |
| EP | 3031925 A1 | 6/2016 |
| WO | 03015726 A1 | 2/2003 |
| WO | 3015726 A1 | 2/2003 |
| WO | 2014060405 A2 | 4/2014 |

OTHER PUBLICATIONS

Sonnenborn "Baby Mineral Sunscreen Stick with Sonnenatural H-203".

* cited by examiner

*Primary Examiner* — Zohreh A Fay

(57) ABSTRACT

A sunscreen composition having improved water resistance comprising (i) a sunscreen active agent; (ii) a water resistant agent comprising a natural wax having a Damping Factor of less than 1.0 in a linear viscoelastic range at body temperature; and (iii) an emulsifier or a surfactant capable of stabilizing an emulsion of components (i) to (iii), wherein said sunscreen composition maintains at least 75%, preferably at least 85%, and most preferably at least 99%, of its static SPF after water immersion for 4 hours.

18 Claims, 4 Drawing Sheets

Example 1:
Before water submersion    After water submersion

Example 2:
Before water submersion    After water submersion

SUNSCREEN COMPOSITIONS WITH NATURAL WAXES FOR IMPROVED WATER RESISTANCE

BACKGROUND OF THE INVENTION

Field of Endeavor

The present disclosure relates to sunscreen compositions comprising a biodegradable water resistant agent comprising naturally occurring waxes that provides enhanced water resistance, improved spreadability, and low ocular irritation.

Background Information

Natural waxes have been broadly mentioned for use in cosmetic preparations such as face creams or lotions, including over-the-counter dermatological preparations such as sunscreen compositions or other topical compositions. It can also serve as an emollient or film former. However, a review of the prior art by one of ordinary skill in the art finds a paucity of enabling examples.

SUMMARY OF THE INVENTION

The present disclosure is directed, in a first embodiment, to a sunscreen composition comprising (i) 0.1 wt. % to 45 wt. % of a sunscreen active agent; (ii) 0.1 wt. % to 30 wt. % of a water resistant agent comprising one or more natural waxes having a Damping Factor of less than 1.0 as calculated using an oscillation amplitude sweep test conducted from 0.01% to 100% strain at a constant angular frequency of 10 Rad/sec and a temperature of 37° C. wherein a storage modulus of the water resistant agent is higher than a loss modulus of the water resistant agent; and (iii) 0.1 wt. % to 10 wt. % of an emulsifier or a surfactant, wherein said sunscreen composition maintains at least 75% of its static SPF after water immersion for 4 hours.

Preferably, the sunscreen active agent comprises one or more of dibenzoylmethane, terephthalylidene dicamphor sulfonic acid, bis-disulizole disodium, disodium phenyl dibenzimidazole tetrasulfonate, diethylamine hydroxybenzoyl hexylbenzoate, bis-diethylamine hydroxybenzoyl benzoate, bis-benzoxazolylphenyl ethylhexylamino triazine, octocrylene, octinoxate, octisalate, homosalate, ensulizole, ethylhexyl triazone, enzacamene, amiloxate, diethylhexyl butamido triazine, benzylidene malonate polysiloxane, padimate-O, trolamine salicylate, cinoxate, p-aminobenzoic acid, oxybenzone, meradimate, titanium dioxide, zinc oxide, bis-octrizole, bemotrizinol, drometrizole trisiloxane, sulisobenzone, dioxybenzone, encapsulated UV filters, and combinations thereof.

In any of the disclosed embodiments, the water resistant agent is present in an amount of 0.5 wt. % to 5 wt. %. In any of the preceding embodiments, the water resistant agent may further comprise esters of triacylglycerol, diacylglycerol, and/or monoacylglycerol with saturated or unsaturated fatty acids such as palmitic and/or myristic acid. In any of the preceding embodiments, the water resistant agent comprises one or more natural waxes having a pour point of 30° C. to 65° C., selected from the group consisting of myrica wax, china wax, beeswax, shellac wax, shea butter, cocoa butter; and combinations thereof.

In any of the disclosed embodiments, the emulsifier comprises a water-in-oil emulsifier having a hydrophilic-lipophilic balance of less than 6, preferably 4 to 6. The water-in-oil emulsifier is selected from the group consisting of sucrose distearate, sorbitan oleate, sorbitan dioleate, sorbitan stearate; polyglyceryl-4 isostearate, polyglyceryl dimerate isostearate, cetyl PEG/PPG 10/1 dimethicone, lauryl PEG-8 dimethicone, glyceryl stearate, and combinations thereof.

In any of the disclosed embodiments, the emulsifier comprises an oil-in-water emulsifier having a hydrophilic-lipophilic balance of greater than 8, preferably from 9 to 10. The oil-in-water emulsifier is selected from the group consisting of sucrose stearate, sucrose laurate, sorbitan laurate, polyglyceryl-3 methylglucose distearate, and combinations thereof.

Preferably, the surfactant is an ionic surfactant comprising phosphoric acid fatty esters such as dicetyl phosphate, ceteth-10 phosphate, beheneth-30 phosphate, diethanolamine cetyl phosphate, potassium cetyl phosphate, trilaureth-4 phosphate, triceteareth-4 phosphate. Alternatively, the surfactant comprises of other carboxylic acid fatty esters such as sodium stearoyl glutamate, disodium stearoyl glutamate, distearyldimonium chloride, polyquaternium 39, polyquaternium-7, or a combination thereof.

BRIEF DESCRIPTION OF THE DRAWINGS

The features of the disclosure believed to be novel and the elements characteristic of the invention are set forth with particularity in the appended claims. The figures are for illustration purposes only and are not drawn to scale. The disclosure itself, however, both as to organization and method of operation, can best be understood by reference to the description of the preferred embodiment(s) which follows, taken in conjunction with the accompanying drawings in which:

DETAILED DESCRIPTION OF THE INVENTION

Figure 1:
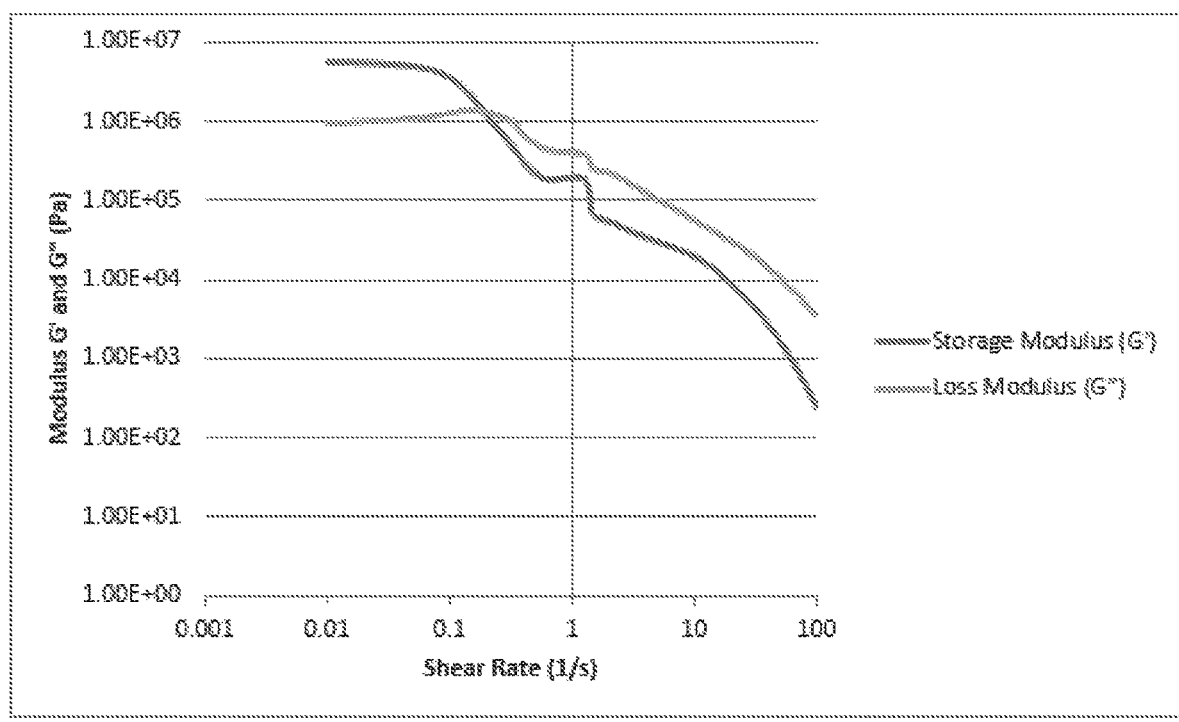
FIG. 1 is a graph showing the rheological data of a mixture of 70 wt. % myrica wax and 30 wt. % triglycerides illustrating the desirable elasticity of a water resistant agent.

The embodiments of the present disclosure can comprise, consist of, and consist essentially of the features and/or steps described herein, as well as any of the additional or optional ingredients, components, steps, or limitations described herein or would otherwise be appreciated by one of skill in the art. It is to be understood that all concentrations disclosed herein are by weight percent (wt. %.) based on a total weight of the composition unless otherwise indicated. Where appropriate, the INCI (International Nomenclature of Cosmetic Ingredients) name of ingredients components is provided. Any numerical range recited herein is intended to include all sub-ranges subsumed therein, and such ranges are understood to include each and every number and/or fraction between the stated range lower and upper values.

The present disclosure is directed to sunscreen compositions having improved water resistance comprising (i) an effective amount of a sunscreen active agent; (ii) a water resistant agent comprising a natural wax; and (iii) an emulsifier or surfactant capable of sustaining an emulsion of the sunscreen active and the water proofer comprising the natural wax. The inventive compositions of the present disclosure provide water resistance up to, and possibly beyond, four (4) hours when evaluated using the in vivo Australian/New Zealand Standard 2604:2012 and ISO 2444 (2010) Four Hour Water Resistance test. It has increased spreadability and reduced stickiness, while safe for sensitive skin and does not cause lacrimation.

(i) Sunscreen Active Agents

The one or more sunscreen active agents useful in the present invention, are capable of attenuating all or part of the harmful effects of ultraviolet ("UV") radiation. In addition, the sunscreen active agents must be non-toxic and non-irritating when applied to the skin. Sunscreen active agents are, typically, categorized into four groups, as follows.

A first group of sunscreen active agents includes ultraviolet A long-wave or "UVA" sunscreen active agents. UVA sunscreen active agents, for example, include a member selected from the group consisting of avobenzone, terephthalylidene dicamphor sulfonic acid, bis-disulizole disodium, disodium phenyl dibenzimidazole tetrasulfonate, diethylamine hydroxybenzoyl hexylbenzoate, bis-diethylamine hydroxybenzoyl benzoate, bis-benzoxazolylphenyl ethylhexylamino triazine, and combinations thereof.

A second group of sunscreen active agents include ultraviolet B shortwave or "UVB" sunscreen active agents. UVB sunscreen active agents, for example, include a member selected from the group consisting of octocrylene, octinoxate, octisalate, homosalate, ensulizole, ethylhexyl triazone, enzacamene, amiloxate, diethylhexyl butamido triazine, benzylidene malonate polysiloxane, padimate-O, trolamine salicylate, cinoxate, p-aminobenzoic acid, derivatives thereof, and combinations thereof.

A third group of sunscreen active agents include sunscreen active agents that absorb both UVA and UVB radiation. These full spectrum UV active agents include a member selected from the group consisting of, for example, oxybenzone, meradimate, titanium dioxide, zinc oxide, bis-octrizole, bemotrizinol, drometrizole trisiloxane, sulisobenzone, dioxybenzone, and combinations thereof.

Further, useful sunscreen active agents that reflect or scatter UV radiation include titanium dioxide, zinc oxide, surface treated titanium dioxide, surface treated zinc oxide, and a combination thereof. Examples of the mineral based sunscreens are Microtitanium Dioxide MT™, UV-titan M262™, Parsol TX™, JTTO-MS7™, Z-Cote™, ZanoT™, Zano M™, Zano 10™, Zano 10 plus™, and a combination thereof.

The fourth group of sunscreen active agents include encapsulated UV filters. Encapsulated UV filters include a member selected from the group consisting of AVOCAP™ (encapsulated Avobenzone 60% payload and 15% of Octocrylene), OMCCAP™ (encapsulated Octyl Methoxycinnamate, 60% payload), OXYCAP™ (encapsulated Oxybenzone, 47% payload and Octocrylene 20%), HOMCAP™ (encapsulated Homosalate, 60% payload), OCTICAP™ (encapsulated Octisalate 60% payload), ZINOCAP™ (encapsulated ZnO, 70% payload), TITANCAP™ (encapsulated TiO2: 70% payload).

The selection of one or more sunscreen active agents, for use in a sunscreen embodiment of the invention, is made in accordance with the desired objectives for the final product, i.e., sun protection factor (SPF), broad spectrum protection, etc. For example, consumers often desire a full spectrum of UV protection to lessen the risk of cancer and accelerated skin aging from prolonged sun exposure. Some consumers desire a limited exposure of UV radiation to acquire some tanning effects from sun exposure, while minimizing the risk of burning.

The sunscreen active agents are present, either alone or in combination, in an amount of about 0.1 wt. % to about 45 wt. %, preferably from about 2 wt. % to about 40 wt. %, and most preferably from about 6.5 wt. % to about 30 wt. %, based on a total weight of the composition.

(ii) Water Resistance Agent

The water resistance agent of the inventive compositions is preferably biodegradable comprising a natural wax. The water resistance agent has a melting point that is below 80° C., preferably below 70° C., and most preferably below 60° C. A combination of water resistance agents can be used to lower the melting point of the mixture to the desired range. For example only, a mixture of natural waxes can be used that provide a melting point that is below 80° C., preferably below 70° C., and most preferably below 60° C. Additionally, other synthetic waxes may be added to lower the melting point of the water resistance agent.

Preferably, the water resistance agent has a strong mechanical strength due to its elastic-like structure as measured using the oscillation amplitude sweep test method by the Anton Paar MCR 301 rheometer. The oscillation amplitude sweep test was conducted from 0.01% to 100% strain at a constant angular frequency of 10 Rad/sec and a constant temperature of 37° C. The dynamic storage and loss modulus (G' and G") were plotted against shear strain ($\gamma$) in the rheological graph. The Damping Factor (tan $\delta$), the ratio of loss modulus to a storage modulus, can be expressed as follows:

$$\text{Damping Factor (tan } \delta) = G''/G'$$

The structure of the water resistant agent exhibits a more elastic behavior if the storage (G') is higher than the loss modulus (G") and the Damping Factor is less than 1.0, whereas the structure of the water resistance agent exhibits a more viscous behavior if the storage modulus (G') is lower than the loss modulus (G") and the Damping Factor is greater than 1.0. For example only, the Damping Factor of a preferred water resistant agent, myrica wax, is less than 1.0 in the linear viscoelastic range when the strain is less than 0.1%. FIG. 1 shows the rheological data of a mixture of 70 wt. % myrica wax and 30 wt. % triglycerides. The triglycerides were added to aid in test performance. The myrica wax/triglyceride mixture shows a desirable elasticity for use in the inventive compositions Examples of the water resistant agent in the sunscreen composition are natural plant waxes, animal waxes, and their derivatives; such as myrica wax (also known as bayberry wax), china wax, beeswax, shellac wax, shea butter, cocoa butter, or a combination thereof. The water resistant agent may further include the esters of triacylglycerol, diacylglycerol, and/or monoacylglycerol with saturated or unsaturated fatty acids, preferably palmitic and myristic acids. A single water resistant agent can provide the desired Damping Factor or a plurality of the water resistant agents can be combined to form the desired elastic profile.

The water resistant agent is preferably present in an amount of 0.1 wt. % to 30 wt. %, more preferably, 0.5 wt. % to 20 wt. %, and most preferably from 0.5 wt. % to 5 wt. %. Any amounts in between the ranges stated above are also viable to produce a satisfactory composition with the desired water resistance and skin feel.

(iii) Emulsifier or Surfactant

The inventive compositions further include an emulsifier or surfactant. Preferably, the emulsifier includes at least a water-in-oil (W/O) emulsifier, and oil-in-water (O/W) emulsifier, a nonionic surfactant, or a combination thereof, in an amount that effectively stabilizes the emulsion. Preferably, the emulsifier or surfactant may be present in an amount of about 0.1 wt. % to about 10 wt. %, more preferably from about 1 wt. % to about 8 wt. %, and most preferably from about 2 wt. % to about 6 wt. %, based on a total weight of the composition.

The W/O emulsifier is useful to stabilize the emulsion wherein the water phase is dispersed in a continuous oil phase. Preferably, a W/O emulsifier has a hydrophilic-lipophilic balance (HLB) of less than 6, preferably from 4 to 6. Examples of water-in-oil emulsifiers having a HLB of less than 6 include sucrose esters such as sucrose distearate; sorbitan esters such as sorbitan oleate, sorbitan dioleate, sorbitan stearate; polyglyceryl esters such as polyglyceryl-4 isostearate, polyglyceryl dimerate isostearate; cetyl polyethylene glycol (PEG)/polypropylene glycol (PPG) 10/1 dimethicone; lauryl polyethylene glycol-8 (PEG-8) dimethicone; glyceryl stearate; or a combination thereof.

The O/W emulsifier is useful to stabilize the emulsion wherein the oil phase is dispersed in a continuous water phase. The oil-in-water emulsifier preferably has a HLB of greater than 7, preferably 7 to 9 or 10. Examples of oil-in-water emulsifiers include other sucrose esters such as sucrose stearate, sucrose laurate; sorbitan esters such as sorbitan laurate; polyglyceryl-3 methylglucose distearate; or a combination thereof. Alternatively, ethoxylated fatty ethers and ethoxylated fatty esters may be useful as oil-in-water emulsifiers having a HLB greater than 8.

The surfactants useful in stabilizing the emulsion can be either an anionic surfactant or a cationic surfactant. Ionic surfactants have better affinity to skin than nonionic surfactants. Examples of ionic surfactants are phosphoric acid fatty esters such as dicetyl phosphate, ceteth-10 phosphate, beheneth-30 phosphate, diethanolamine cetyl phosphate, potassium cetyl phosphate, trilaureth-4 phosphate, triceteareth-4 phosphate, or a combination thereof. Other ionic surfactants may comprise carboxylic acid fatty esters such as sodium stearoyl glutamate, disodium stearoyl glutamate, distearyldimonium chloride, polyquaternium-39, polyquaternium-7, or a combination thereof.

Other Ingredients

The sunscreen composition may further include one or more active or inactive cosmetic ingredients, such as, but not limited to, cosmetically acceptable carriers; oils; sterols; amino acids; moisturizers; powders; colorants (including pigments and/or dyes); pH adjusters; perfumes; essential oils; cosmetic active ingredients; essential fatty acids; sphingolipids; self-tanning compounds such as dihydroxyacetone (DHA) and erythruloses; fillers; emulsifying agents; antioxidants; surfactants; additional film formers; chelating agents; gelling agents; thickeners; emollients; humectants; moisturizers; minerals; viscosity and/or rheology modifiers; keratolytics; retinoids; hormonal compounds; alpha-keto acids; anti-mycobacterial agents; anti-fungal agents; anti-microbials; anti-virals; analgesics; anti-allergenic agents; H1 or H2 antihistamines; anti-inflammatory agents; anti-irritants; anti-neoplastics; immune system boosting agents; immune system suppressing agents; anti-acne agents; anesthetics; antiseptics; insect repellents; skin cooling compounds; skin protectants; skin penetration enhancers; exfoliants; lubricants; staining agents; depigmenting agents; hypopigmenting agents; preservatives; stabilizers; pharmaceutical agents; photostabilizing agents; spherical powders; one or more fragrances; plant extracts; absorbents; salicylic acid; alpha and beta hydroxy acids; vitamins including vitamins A, C, and E; retinol and its derivatives; or any combination of the foregoing. One of ordinary skill in the art can appreciate and understand that this list is not limiting, and that various other active or inactive ingredients may be used in the present inventive compositions.

The following formulations were prepared using the inventive compositions as shown in Table I below.

TABLE I

| INCI NAME | Ex. 1 | Ex. 2 | Ex. 3 |
|---|---|---|---|
| DI Water | | Q.S. to 100 | |
| Isohexadecane | | 15-30 | |
| Homosalate | | 8-15 | |
| Octocrylene | | 5-10 | |
| Octisalate | | 5-10 | |
| Avobenzone | | 1-5 | |
| Ethylhexyl Benzoate | | 3-6 | |
| Cetyl PEG/PPG-10/1 Dimethicone | | 2-4 | |
| Lauryl PEG-8 Dimethicone | | 1.5-3.5 | |
| Ethylhexyl Methoxycrylene | | 1-3 | |
| Caprylyl Glycol | | 0.50-1.5 | |
| Glycerin | | 0.5-2.0 | |
| Phenoxyethanol | | 0.5-1.0 | |
| Sodium Chloride | | 0.5-1.5 | |
| Sodium Citrate | | 0.08-1.5 | |
| Water resistant agent | | 0.5-5.0 | |
| Acrylates/$C_{12-22}$ Alkyl methacrylate copolymer and water | | | 0.5-5.0 |

Example 1 is a spray lotion with a similar formula to commercially available BANANA BOAT® Tear-Free Sting-Free Spray Lotion. Example 2 is an inventive composition wherein myrica wax is the water resistant agent. Example 3 is a comparative example using a conventional film former such as Acrylates/$C_{12-22}$ Alkyl methacrylate copolymer as a water resistant agent.

Figure 2:
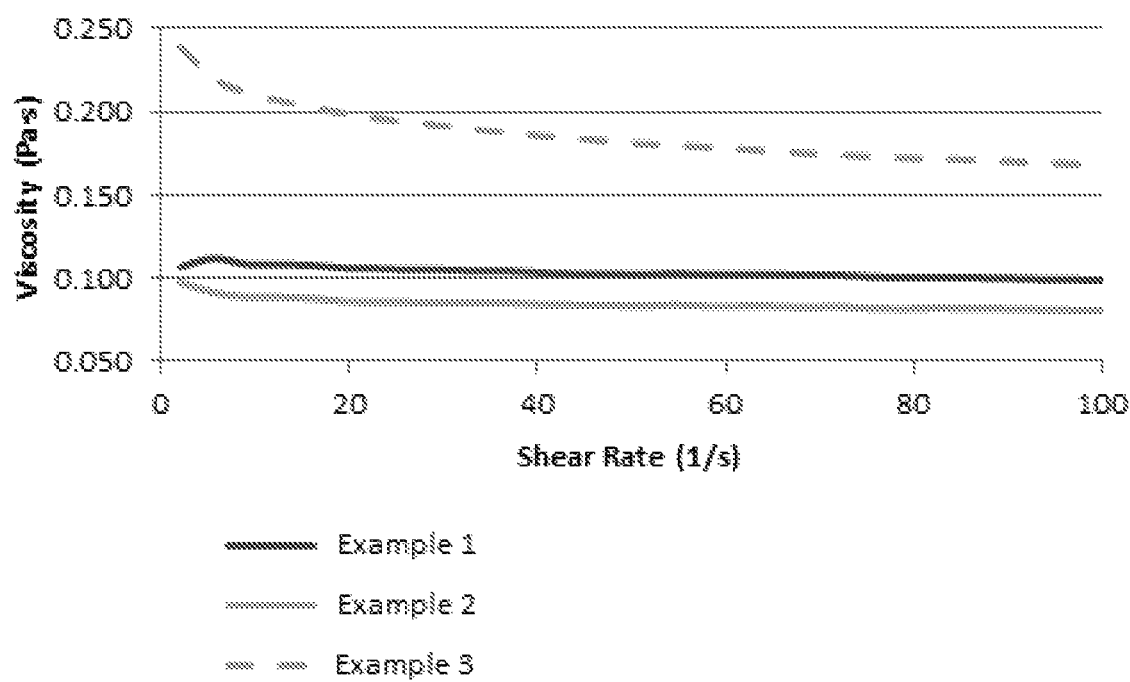
FIG. 2 is a graph showing the flow curve of compositions Examples 1 to 3 plotting viscosity versus shear rate to illustrate the desired viscosity as it relates to a preferred dispensing profile.

The inventive composition of Example 2 shows improved spreadability with the addition of the water resistant agent such that the viscosity of the composition is not changed significantly at a constant shear rate. FIG. 2 is the flow curve of compositions Examples 1 to 3. FIG. 2 plots viscosity against shear rate using the linear shear ramp (2-100 $S^{-1}$) stepwise method at a constant shear rate of 5 $S^{-1}$ using the Anton Paar MCR 301 rheometer. Low shear rate behavior can be related to the storage conditions of a formulation and high shear rate behavior can be related to the dispensing conditions of a formulation. A conventional film former in Example 3 shows a significantly increased viscosity of the composition with the conventional film former producing an uneven dispensing profile as a result. The inventive composition of Example 2 causes very little or no change to the viscosity of the composition with the addition of the water resistant agent and has an even dispensing profile as a result.

Figure 3:
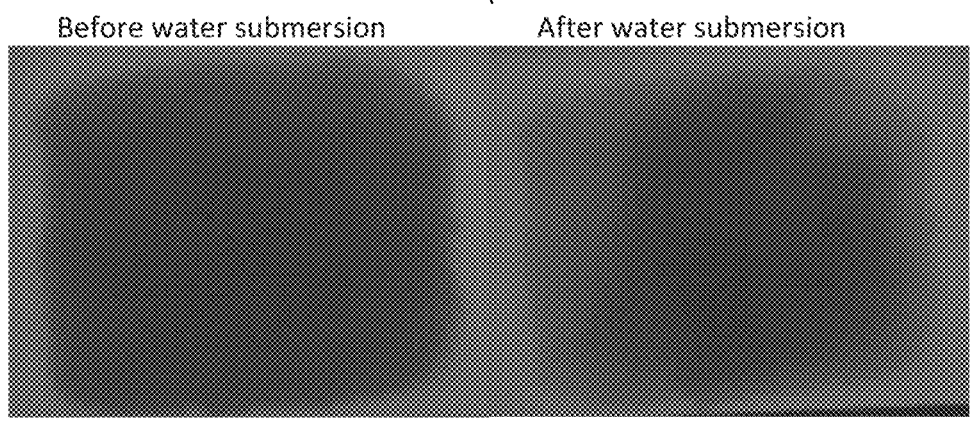
FIG. 3 are photographs taken under ultraviolet light of Examples 1 and 2 before and after water immersion.
Figure 3:
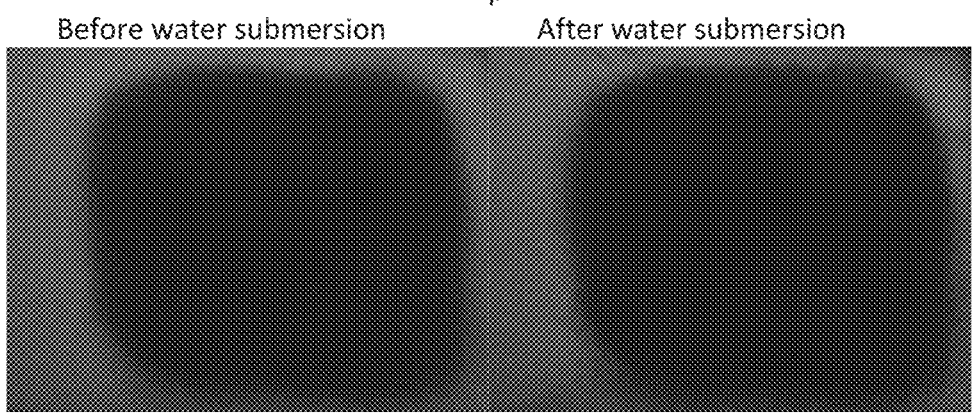

The inventive compositions also show an unexpected uniformity in application resulting in a more even distribution of sunscreen active agents on and adherence to the skin after exposure to water. Examples 1 and 2 were uniformly applied to VITRO-SKIN® plates, commercially available from IMS, Inc., Portland, Me., by finger with a pre-saturated finger cot at a dose of 2 mg/cm² according to the method stated in ISO24443:2012. The VITRO-SKIN was air-dried (e.g., for about 15 minutes). The VITRO-SKIN was pre-hydrated by following the manufacturer's recommendation. After drying, the samples were immersed in tap water for two (2) hours with slow agitation by a propeller at the speed of 150 rpm and at a temperature of 30° C. Examination under UV light before and after water immersion shows the distribution of sunscreen actives on the VITRO-SKIN. In FIG. 3, the upper left square is a photo of Example 1, a conventional composition, prior to water submersion. The upper right square is a photo of Example 1 after water submersion. After water submersion, the edges of Example 1 are less defined and the area of application is diminished due to some of the composition washing off. The lower left square is a photo of Example 2, containing the water resistant agent, prior to water submersion. The lower right square is a photo of Example 2 after water submersion. There is little difference is the photos before and after water submersion indicating a more uniform application with little to no wash off of the sunscreen composition.

Figure 4:
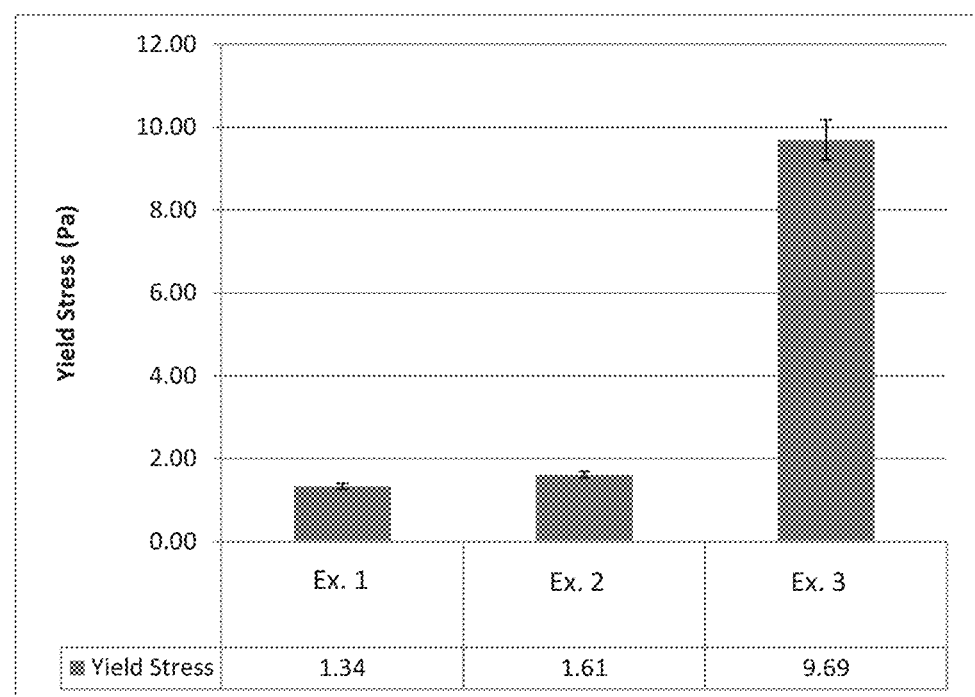
FIG. 4 is a bar graph showing the average yield stress from three (3) samples each of Examples 1 to 3.

The unique rheology profile of the inventive compositions provides better spreadability than conventional sunscreen compositions that use a synthetic water resistant agent. Yield stress is a critical stress where the composition starts to break and flow. It can be measured using the linear stress ramp stepwise method with a rotation shear stress from 0.1 to 10 Pa and a constant shear rate of 5 $S^{-1}$ using the Anton Paar MCR 301 rheometer. The yield stress is an important rheological measurement used as an indication of the ease with which a formulation can be spread on the skin. The lower the yield stress, the higher the spreadability of the composition. The inventive compositions have very little effect on the yield stress in comparison to Example 3 that contains a synthetic water resistant agent as shown in FIG. 4. Example 2 shows a yield stress that is comparable to Example 1 that does not contain any type of water resistant agent or film former whereas the composition of Example 3 has a significantly higher yield stress. A high yield stress indicates low spreadability, an undesirable trait in sunscreen compositions.

In vivo water resistance was measured on ten (10) subjects using the methodology disclosed in the Australia/New Zealand standard 2604:2012 and ISO 24444 2010 for four (4) hours water resistance showed the improved water resistance of the inventive compositions. An SPF of at least 60 was successfully maintained for at least four (4) hours as shown in Table II.

TABLE II

| Subject No. | SPF (P3) Standard | SPF 15 15/15 WR Control | Example 2 - SPF Values | |
|---|---|---|---|---|
| | | | Static | After Submersion |
| 1 | 15.0 | 15.0 | 72.7 | 72.7 |
| 2 | 18.8 | 15.0 | 72.8 | 65.0 |
| 3 | 18.8 | 18.8 | 72.8 | 72.8 |
| 4 | 18.7 | 18.7 | 65.0 | 65.0 |
| 5 | 18.8 | 15.0 | 72.8 | 65.0 |
| 6 | 15.0 | 15.0 | 72.7 | 72.7 |
| 7 | 15.0 | 15.0 | 65.0 | 65.0 |
| 8 | 18.8 | 18.8 | 72.8 | 72.8 |
| 9 | 15.0 | 15.0 | 65.0 | 65.0 |
| 10 | 18.8 | 15.0 | 72.8 | 65.0 |

SPF (P3) is a control lotion that is used in the Australia/New Zealand protocol, and Table II lists the in vivo SPF for the control in column 2. In the second column, SPF 15 is the control lotion after water submersion. Example 2 shows SPF values maintained throughout the four (4) hour test with a slight reduction in SPF after water submersion in a minority of subjects.

The sunscreen compositions of the present invention may also be formulated as a concentrate with a propellant to provide a continuous spray commercial product. The propellant generally exists as equilibrium of vapor and liquid and can be either dissolved in or miscible with the composition. Examples of suitable propellants are isobutene, butane, propane, dimethyl ether, methyl ether, or a combination thereof. The aerosol propellant may comprise about 10 wt. % to 60 wt. %, based on a total weight of the final composition. Alternatively, a bag-on-valve system may be used to deliver the sunscreen composition using compressed gas such as air, nitrogen, or carbon dioxide to deliver the composition onto the skin.

While the present disclosure has been particularly described, in conjunction with specific preferred embodiments, it is evident that many alternatives, modifications, and variations will be apparent to those skilled in the art in light of the foregoing description. It is therefore contemplated that the appended claims will embrace any such alternatives, modifications, and variations as falling within the true scope and spirit of the present disclosure.

What is claimed is:

1. A sunscreen composition comprising:
   (i) 0.1 wt. % to 45 wt. % of a sunscreen active agent;
   (ii) 0.1 wt. % to 5 wt. % of a water resistant agent comprising myrica wax;
   (iii) 0.1 wt. % to 10 wt. % of an emulsifier comprising cetyl polyethylene glycol (PEG)/polypropylene glycol (PPG)-10/1 dimethicone and lauryl PEG-8 dimethicone; and
   (iv) 0.5 wt. % to 37.5 wt. % of an emollient.

2. The sunscreen composition of claim 1, wherein said sunscreen active agent comprises one or more of dibenzoylmethane, terephthalylidene dicamphor sulfonic acid, bis-disulizole disodium, disodium phenyl dibenzimidazole tetrasulfonate, diethylamino hydroxybenzoyl hexylbenzoate, bis-diethylamino hydroxybenzoyl benzoate, bis-benzoxazolylphenyl ethylhexylamino triazine, octocrylene, octinoxate, octisalate, homosalate, ensulizole, ethylhexyl triazone, enzacamene, amiloxate, diethylhexyl butamido triazine, benzylidene malonate polysiloxane, padimate-O, trolamine salicylate, cinoxate, p-aminobenzoic acid, oxybenzone, meradimate, titanium dioxide, zinc oxide, bis-octrizole, bemotrizinol, drometrizole trisiloxane, sulisobenzone, dioxybenzone, encapsulated UV filters, or a combination thereof.

3. The sunscreen composition of claim 1, wherein said water resistant agent consists essentially of one or more of plant waxes and animal waxes having a Damping Factor of less than 1.0 calculated using an oscillation amplitude sweep test conducted from 0.01% to 100% strain at a constant angular frequency of 10 Rad/sec and a temperature of 37° C., wherein a storage modulus of the water resistant agent is higher than a loss modulus of the water resistant agent.

4. The sunscreen composition of claim 1, wherein said water resistant agent is present in an amount of 0.5 wt. % to 5 wt. %.

5. The sunscreen composition of claim 4, wherein said water resistant agent further comprises one or more of china wax, beeswax, shellac wax, rhea butter, and cocoa butter.

6. The sunscreen composition of claim 1, wherein said water resistant agent further comprises esters of triacylglycerol, diacylglycerol, and/or monoacylglycerol with palmitic acid or myristic acid.

7. The sunscreen composition of claim 1, wherein said water resistant agent comprises one or more natural waxes having a pour point of 30° C. to 65° C.

8. The sunscreen composition of claim 1, wherein said emulsifier further comprises sucrose distearate, sorbitan oleate, sorbitan dioleate, polyglyceryl-4 isostearate, polyglyceryl dimerate isostearate, glyceryl stearate, or a combination thereof.

9. The sunscreen composition of claim 1, wherein said emulsifier further comprises sucrose stearate, sorbitan laurate, polyglyceryl-3 methylglucose distearate, or a combination thereof.

10. The sunscreen composition of claim 1, further comprising a surfactant.

11. The sunscreen composition of claim 10, wherein said surfactant is an ionic surfactant comprising dicetyl phosphate, ceteth-10 phosphate, beheneth-30 phosphate, diethanolamine cetyl phosphate, potassium cetyl phosphate, trilaureth-4 phosphate, triceteareth-4 phosphate, distearyldimonium chloride, polyquaternium-39, polyquaternium-7, or a combination thereof.

12. The sunscreen composition of claim 1, wherein said emollient comprises one or more of isohexadecane, caprylyl glycol, and ethylhexyl benzoate.

13. The sunscreen composition of claim 12, further comprising 15 wt. % to 30 wt. % of isohexadecane, 0.5 wt. % to 1.5 wt. % of caprylyl glycol, and % 3.0 wt. to 6.0 wt. % of ethylhexyl benzoate.

14. The sunscreen composition of claim 1, further comprising a humectant.

15. The sunscreen composition of claim 14, wherein said humectant comprises glycerin.

16. The sunscreen composition of claim 15, further comprising 0.5 wt. % to 2.0 wt. % of glycerin.

17. The sunscreen composition of claim 1, further comprising a propellant.

18. The sunscreen composition of claim 17, wherein said propellant comprises one or more of isobutene, butane, propane, dimethyl ether, and methyl ether.

\* \* \* \* \*